United States Patent
LeBoeuf et al.

(10) Patent No.: US 6,632,887 B2
(45) Date of Patent: Oct. 14, 2003

(54) COATING COMPOSITIONS AND METHODS FOR REDUCING EDGE GLARE IN IMPLANTABLE OPHTHALMIC LENSES

(75) Inventors: Albert R. LeBoeuf, Burleson, TX (US); John W. Sheets, Jr., Fort Worth, TX (US)

(73) Assignee: Alcon Universal Ltd., Hunenberg (CH)

( * ) Notice: Subject to any disclaimer, the term of this patent is extended or adjusted under 35 U.S.C. 154(b) by 0 days.

(21) Appl. No.: 10/109,809

(22) Filed: Mar. 29, 2002

(65) Prior Publication Data

US 2002/0149741 A1 Oct. 17, 2002

Related U.S. Application Data

(62) Division of application No. 09/730,969, filed on Dec. 6, 2000, now Pat. No. 6,406,739.
(60) Provisional application No. 60/175,779, filed on Jan. 12, 2000.

(51) Int. Cl.[7] ............... C09D 133/08; C09D 133/10; C09D 133/06
(52) U.S. Cl. ............... 525/203; 525/205; 525/218; 525/219; 525/223; 524/516; 524/521; 524/523
(58) Field of Search ............... 525/203, 205, 525/218, 219, 223; 524/516, 521, 523

(56) References Cited

U.S. PATENT DOCUMENTS

| | | | |
|---|---|---|---|
| 4,304,895 A | 12/1981 | Loshaek | 526/313 |
| 4,528,311 A | 7/1985 | Beard et al. | 524/91 |
| 4,605,409 A | 8/1986 | Kelman | 623/6 |
| 4,731,079 A | 3/1988 | Stoy | 623/6 |
| 4,771,089 A * | 9/1988 | Ofstead | |
| 4,808,181 A | 2/1989 | Kelman | 623/6 |
| 5,290,892 A | 3/1994 | Namdaran et al. | 526/259 |
| 5,331,073 A | 7/1994 | Weinschenk, III et al. | 526/264 |
| 5,378,763 A * | 1/1995 | Drzewinski | |
| 5,470,932 A | 11/1995 | Jinkerson | 526/312 |
| 5,549,670 A | 8/1996 | Young et al. | 623/6 |
| 5,670,097 A * | 9/1997 | Duan et al. | |
| 5,693,093 A | 12/1997 | Woffinden et al. | 623/6 |
| 5,693,095 A | 12/1997 | Freeman et al. | 623/6 |
| 5,698,192 A | 12/1997 | Goldberg | 424/78.18 |
| 5,755,786 A | 5/1998 | Woffinden et al. | 623/15 |
| 5,769,889 A | 6/1998 | Kelman | 623/6 |
| RE36,150 E | 3/1999 | Gupta | 623/6 |
| 6,045,577 A | 4/2000 | Woffinden et al. | 623/5 |

FOREIGN PATENT DOCUMENTS

| | | |
|---|---|---|
| EP | 0 834 352 A1 | 4/1998 |
| WO | WO 99/07309 | 2/1999 |

OTHER PUBLICATIONS

Koch, D. Foldable Intraocular Lenses, Slack Incorporated, Thorofare, NJ (1993), Chapters 8–12, pp. 161–219.

Walheim et al., "Nanophase–Separated Polymer Films as High–Performance Antireflection Coatings," Science, vol. 283, pp. 520–522 (1999).

* cited by examiner

*Primary Examiner*—David J. Buttner
(74) *Attorney, Agent, or Firm*—Patrick M. Ryan

(57) ABSTRACT

Hydrophilic coatings for implantable ophthalmic lenses are disclosed. The coatings, which are applied to the edge surface of the ophthalmic lens, comprise a hydrophobic (meth)acrylic polymer and a hydrophilic polymer. When hydrated, the coatings reduce or eliminate edge glare.

1 Claim, No Drawings

COATING COMPOSITIONS AND METHODS FOR REDUCING EDGE GLARE IN IMPLANTABLE OPHTHALMIC LENSES

This application is a divisional of U.S. Ser. No. 09/730,969 filed Dec. 6, 2000 now U.S. Pat. No. 6,406,739, which claims priority to U.S. Provisional Application, U.S. Ser. No. 60/175,779 filed Jan. 12, 2000.

FIELD OF THE INVENTION

This invention relates to coatings for implantable ophthalmic lenses. In particular, the present invention relates to hydrophilic coatings that are applied to the edge of implantable ophthalmic lenses.

BACKGROUND OF THE INVENTION

Both rigid and foldable implantable ophthalmic lens materials are known. The most common rigid material used in ophthalmic implants is polymethyl methacrylate ("PMMA"). Foldable intraocular lens ("IOL") materials can generally be divided into three categories: silicone materials, hydrogel materials, and non-hydrogel ("hydrophobic") (meth)acrylic materials. See, for example, *Foldable Intraocular Lenses,* Ed. Martin et al., Slack Incorporated, Thorofare, N.J. (1993). For purposes of the present application, hydrophobic (meth)acrylic materials are (meth)acrylic materials that absorb less than approximately 5% water at room temperature.

As described in U.S. Pat. No. 5,755,786, IOLs, particularly IOLs designed for implantation through a small incision, can suffer from a problem of edge glare. The invention described in the '786 patent reduces edge glare by including means, such as a plurality of v-shaped grooves, on the optic edge's surface for reflecting visible light that contacts the edge surface away from the retina of the patient.

Other methods of reducing edge glare include those described in U.S. Pat. Nos. 5,693,093; 5,769,889; 4,808,181; and 4,605,409.

SUMMARY OF THE INVENTION

The present invention relates to hydrophilic coating compositions for surgical implants, particularly ophthalmic implants comprising silicone or hydrophobic (meth)acrylic materials. More specifically, the present invention relates to a coating material comprising an ophthalmically acceptable hydrophobic (meth)acrylic polymer and an ophthalmically acceptable hydrophilic polymer.

The present invention also relates to a method for reducing edge glare in implantable ophthalmic lenses. The method comprises applying a coating comprising an ophthalmically acceptable hydrophobic (meth)acrylic polymer and an ophthalmically acceptable hydrophilic polymer to an implant's optic edge surface. When hydrated, the coating is hazy or opaque and reduces or eliminates edge glare.

DETAILED DESCRIPTION OF THE INVENTION

Unless indicated otherwise, all amounts are expressed as % (w/w).

As used herein hydrophobic "(meth)acrylic polymer" means a hydrophobic methacrylic polymer, a hydrophobic acrylic polymer, or a hydrophobic copolymer containing both methacrylic and acrylic functional groups. As used herein, "hydrophobic" means the materials absorb less than approximately 5% water at room temperature.

The coating material of the present invention comprises an ophthalmically acceptable hydrophobic (meth)acrylic polymer and a hydrophilic polymer. When hydrated, the coating material has a $T_g$ less than 37° C., and preferably less than 15° C. The hydrophobic (meth)acrylic polymer ingredient in the coating material is preferably tacky to aid in attaching the coating material to the substrate. Many ophthalmically acceptable hydrophobic (meth)acrylic polymers are known, including those described in U.S. Pat. Nos. 5,290,892; 5,693,095; and 5,331,073, the entire contents of which are hereby incorporated by reference. Although aliphatic (meth)acrylate monomers can be used to form the hydrophobic (meth)acrylic polymer, the hydrophobic (meth)acrylate polymer preferably comprises at least one (meth)acrylic monomer that contains an aromatic group, such as those materials defined in U.S. Pat. No. 5,693,095:

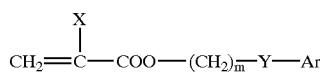

wherein:
 X is H or $CH_3$;
 m is 0–6;
 Y is nothing, O, S, or NR, wherein R is H, $CH_3$, $C_nH_{2n+1}$ (n=1–10), iso-$OC_3H_7$, $C_6H_5$, or $CH_2C_6H_5$; and
 Ar is any aromatic ring which can be unsubstituted or substituted with $CH_3$, $C_2H_5$, n-$C_3H_7$, iso-$C_3H_7$, $OCH_3$, $C_6H_{11}$, Cl, Br, $C_6H_5$, or $CH_2C_6H_5$.

Suitable hydrophobic (meth)acrylic polymers include copolymers of 2-phenylethyl methacrylate (2-PEMA) and 2-phenylethyl acrylate (2-PEA).

After selecting the (meth)acrylic monomer(s), the hydrophobic (meth)acrylic polymer is formed using an initiator (generally about 2% or less). Any type of polymerization initiator may be used, including thermal initiators and photoinitiators. A preferred initiator is the benzoylphosphine oxide initiator, 2,4,6-trimethyl-benzoyldiphenylophosphine oxide ("TPO"), which can be activated by blue light or UV irradiation. Suitable thermal initiators include the conventional peroxides t-butyl peroctoate and bis-azoisobutronitrile. Suitable UV initiators include benzoin methyl ether, Darocur 1173, and Darocur 4265 UV initiators.

The hydrophobic (meth)acrylic polymer optionally contains one or more ingredients selected from the group consisting of UV absorbers that are copolymerizable with the other (meth)acrylic ingredients; blue-light blocking colorants that are copolymerizable with the other (meth)acrylic ingredients; and chain transfer agents to minimize cross-linking.

Ultraviolet absorbing chromophores can be any compound which absorbs light having a wavelength shorter than about 400 nm, but does not absorb any substantial amount of visible light. Suitable copolymerizable ultraviolet absorbing compounds are the substituted 2-hydroxybenzophenones disclosed in U.S. Pat. No. 4,304,895 and the 2-hydroxy-5-acryloxyphenyl-2H-benzotriazoles disclosed in U.S. Pat. No. 4,528,311. The most preferred ultraviolet absorbing compound is 2-(3'-methallyl-2'-hydroxy-5'-methyl phenyl) benzotriazole. Suitable polymerizable blue-light blocking chromophores include those disclosed in U.S. Pat. No. 5,470,932. If a blue-light activated polymerization initiator is chosen and a blue-light blocking colorant is added, the polymerization initiator identity or concentration may have to be adjusted to minimize any interference.

Chain transfer agents, if present, are typically added in an amount ranging from 0.01 to 0.4%. Many chain transfer agents are known in the art. Examples of suitable chain transfer agents include 1-dodecanethiol and 2-mercaptoethanol.

The hydrophilic polymer contained in the coating materials of the present invention may be any ophthalmically acceptable hydrophilic polymer. Suitable hydrophilic polymers include, but are not limited to polyhydroxyethyl methacrylate (polyHEMA); polyacrylamide; polyglyceryl methacrylate and polyvinyl pyrrolidone (PVP). The most preferred hydrophilic polymer is PVP. These hydrophilic polymers are commercially available or can be made using known methods and are preferably obtained in a purified form in order to minimize extractables upon implantation of the coated IOL.

The hydrophilic polymer preferably has a molecular weight (weight avg.) in the range of 2,500–100,000. It is important that the hydrophilic polymer's molecular weight be great enough and be present in the hydrogel coating material in a sufficient amount to form hydrophilic domains capable of dispersing light. The hydrophilic polymer should not be too small, otherwise an appreciable amount of it may leach out of the coating after the coating is applied to the IOL. The hydrophilic polymer should not be too large, otherwise it may affect intraocular pressure in the event that some of the polymer leaches out of the coating. In the case of PVP, a molecular weight of 10,000 is preferred.

The coating material is formed by preparing an ophthalmically acceptable hydrophobic (meth)acrylic polymer, then purifying (if necessary or desired) the cured hydrophobic (meth)acrylic polymer via extraction in a suitable solvent, then dissolving the hydrophobic (meth)acrylic polymer and an ophthalmically acceptable hydrophilic polymer in a suitable solvent or mixture of solvents to form a coating solution. The proportion of hydrophobic (meth)acrylic polymer to hydrophilic polymer in the coating composition depends upon on the desired hydrated water content for the coating, the desired thickness of the coating, the chosen hydrophobic (meth)acrylic and hydrophilic materials, etc. Once the desired coating thickness and water content are chosen, the proportion of hydrophobic (meth)acrylic polymer to hydrophilic polymer can be determined by routine calculations and experimentation. In general, the desired water content of the hydrated coating will range from about 20–70% and the desired coating thickness will range from 0.5–1 $\mu$m. Typical concentrations of hydrophilic polymer in the coating material will therefore range from about 5 to about 50%, preferably from about 15 to about 30%.

The solvent or solvent mixture used to form the coating solution should be chose to give a homogeneous coating solution. Because the coatings will be used to reduce glare, it is not necessary for the coating solution to be clear. Whether or not the coating solution is clear, the coating should be translucent to opaque after being applied to the implant's edge and hydrated. An example of a suitable solvent mixture in the case of a 2-PEMA/2-PEA copolymer as the hydrophobic (meth)acrylic polymer and PVP as the hydrophilic polymer is a 2-pentanone/methanol mixture. In general, polar solvents such as alcohols will be suitable when the hydrophilic polymer is polyHEMA or polyglycerylmethacrylate, and ketones, such as 2-pentanone, or methylene chloride, will be suitable when the hydrophilic polymer is polyacrylamide or PVP.

The coating material is preferably attached to the substrate IOL by means of one or both of the following: (1) hydrophobic or "physical" (i.e., non-covalent) cross-linking and (2) interpenetrating polymer networking. The coating material is internally cross-linked by non-covalent cross-linking. Alternatively, the coating material may be covalently cross-linked to the IOL by means of a cross-linking agent.

The coating solution is applied to the implant's edge surface by conventional techniques, such as spin- or dip-coating processes or casting a coating layer around a pre-formed rod of the optic material. Dip-coating is preferred. The implant is preferably dipped at such a rate so as to minimize any swelling of the implant caused by the solvent in the coating solution.

After the coating is applied to the implant, the coating is dried. A two-stage drying process is preferred. First, the coated implant is allowed to dry in air until most or all of the solvent has evaporated (generally $\leq$15 minutes). Second, the coated implant is baked at elevated temperature, about 40–100° C., to eliminate as much of the remaining solvent as possible. A preferred drying process involves room temperature air drying for 15 minutes, followed by baking at 90° C. for about 20–60 minutes. If a covalent cross-linking agent is added to the coating solution, the coating is dried in a way that fully activates the cross-linking agent.

The coating can be easily removed by a variety of organic solvents or solvent mixtures, including the same solvent used as the base in the preparation of the coating solution. The coating cannot be removed by water, however.

The implants suitable for coating with the hydrophilic coatings of the present invention are preferably made of hydrophobic (meth)acrylic materials, but could also be constructed of silicone or silicone-(meth)acrylic copolymers. Preferred hydrophobic (meth)acrylic materials are those polymeric materials described in U.S. Pat. Nos. 5,290,892 and 5,693,095, the entire contents of which are hereby incorporated by reference. In the case where the implant is an IOL, the coatings of the present invention may be used in conjunction with substrate materials intended for use as a "hard" IOL (that is inserted in an unfolded state) or a "foldable" or "soft" IOL (that is inserted in a folded or compressed state). Suitable IOL materials to be coated include those disclosed in U.S. Pat. Nos. 5,693,095 or 5,331,073. As used herein, "implants" includes contact lenses.

When covalent cross-linking agents are used, it may be necessary or desirable to prepare the implant's surface that will receive the coating by exposing the implant's surface to a reactive plasma gas prior to applying the coating solution. Suitable reactive plasma gases include oxidizing gases, such as oxygen gas. A suitable plasma chamber is the $P^2CIM$ B-Series plasma chamber made by Advanced Plasma Systems, Inc. Using such a chamber, suitable plasma parameters include: power=400 W, plasma gas=oxygen; pressure of the plasma gas=225 mTorr; exposure time=4–6 minutes.

The following examples are intended to be illustrative but not limiting.

Example 1: Mixture of Hydrophobic (Meth)acrylic Polymer and Hydrophilic Polymer.

A copolymer of 2-PEMA (1.5 parts by weight) and 2-PEA (3.24 parts by weight) was prepared using Darocur 4265 (0.06 parts by weight) as an initiator. The copolymer was cured in polypropylene slab molds (10 mm×20 mm×0.9 mm) by exposure to blue light for one hour using a Kulzer Palatray CU blue light unit (12–14 mW/cm$^2$). The cured copolymer (0.8345 g) was then extracted in methanol at room temperature overnight. The extracted copolymer was dried in air, but not stripped of methanol solvent. Once dry, the slabs were dissolved in a mixture of 2-pentanone and methanol to form the following coating solution:

| Ingredient | amount (parts by weight) |
| --- | --- |
| 2-PEMA2-PEA copolymer | 0.88 |
| PVP (10,000 MW) | 0.33 |
| Methanol | 1.38 |
| 2-Pentanone | 12.46 |

Separately, a copolymer comprising 65% 2-PEA; 30% 2-PEMA; 1.8% o-methallyl Tinuvin P; and 3.2% 1,4-butanediol diacrylate was prepared using 1.8% Perkadox-16 as a thermal initiator. This copolymer ("Substrate Copolymer") was cured in the same slab molds described above and then extracted in acetone (overnight, then dried in air for approximately 2 hours, then dried at 100° C. for approximately 2 hours). Also, commercially available ACRYSOF® IOL's were obtained. The slabs and IOLs were then dipped in the coating solution, dried in air for approximately 5–10 minutes, and then baked at 90° C. for 20–90 minutes. The cured coating was optically clear. After hydrating the coating, the coating is translucent/opaque due to the heterogeneous distribution of water within the coating composition. Coating thickness was typically 0.5 to 1 microns. After remaining hydrated for 9 months, the coating's haze or opacity did not appear to have diminished and remained attached to the substrate slab or IOL.

Example 2: Water Content of the Coating Material of Example 1.

To determine the water content of the hydrated coating material used in Example 1, a multi-layer film of the coating solution defined in Example 1 was cast in a polypropylene slab mold. After each layer was applied, it was allowed to dry at room temperature in air before the next layer was added. After four or five layers were made, the multi-layered film was dried at 100° C. for one hour. The dried film was weighed and then placed in de-ionized water at room temperature. The film's weight change was monitored over time. The results are shown in Table 1 below. After 184 hours of hydration, the film was removed from the de-ionized water, weighed, extracted, dried and weighed again. The film gave 5.7% (by weight) extractables and had a water content (hydrated) of 52.6% (weight). The film was replaced in the deionized water for an additional 432 hours (616 hours total hydration time from the beginning of the experiment). The calculated water content at 616 hours was 59.5% (weight).

TABLE 1

| Elapsed Time (hrs) | Slab Weight (g) | Optical Appearance (coating) | % Weight Increase of Slab |
| --- | --- | --- | --- |
| 0 | 0.0475 | clear | 0 |
| 15.5 | 0.0628 | opaque | 24.4 |
| 40 | 0.0702 | opaque | 32.3 |
| 112 | 0.0840 | opaque | 43.4 |
| 184 | 0.0945 | opaque | 49.7 |
| 616 | 0.1106 | opaque | 57.0 |

Example 3: (Comparative Example) Copolymer of Hydrophobic (Meth)acrylic Monomers and Hydrophilic Monomer.

To 3.25 grams of 2-PEA, 1.50 grams 2-PEMA, 1.81 grams N-vinylpyrrolidone, and 0.06 grams of Darocur 4265 were added. The 'pyrrolidone' content of the coating material was the same as that used in the coating material of Example 1 [27.3%:0.33(0.88+0.33)=1.81/(3.25+1.5+1.81+0.06)]. The resulting coating material was cured in the same polypropylene slab molds described in Example 1. A one-hour, blue-light cure was performed using the Palatray CU unit at a flux of 12–14 mW/cm$^2$. The resulting copolymer was dissolved in 2-pentanone to give a coating solution with a 6 wt-% copolymer content.

A pre-extracted (acetone) slab of the Substrate Copolymer of Example 1 was dipped in the coating solution, air-dried at room temperature for 10 minutes, and oven-cured at 90° C. for 75 minutes. The coated slab was placed into deionized water and its hydration properties followed over time. The results are shown in Table 2 below.

TABLE 2

| Elapsed Time (hrs) | Slab Weight (g) | Optical Appearance (coating) | % Weight Increase of Slab |
| --- | --- | --- | --- |
| 0 | 0.2060 | clear | 0 |
| 25 | 0.2151 | clear | 4.2 |
| 96 | 0.2234 | clear | 7.8 |
| 144 | 0.2263 | clear | 8.9 |
| 425 | 0.2333 | clear | 11.7 |

Water content after 425 hours=12.3% (final hydrated weight-final dried weight)/final hydrated weight Aqueous Extractables=0.6%

As shown in Tables 1 and 2, Examples 1 and 3 gave significantly different results. The hydrated PEMA-PVP polymer mixture coating material is opaque and of high water content, while the hydrated, random PEMA-NVP copolymer is clear and has a lower water uptake.

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

We claim:

1. A hydrophilic coating material for a surgical implant wherein the coating material has a $T_g$ less than 37° C. when hydrated and comprises an ophthalmically acceptable hydrophobic (meth)acrylic polymer and an ophthalmically acceptable hydrophilic polymer, and wherein the hydrophobic (meth)acrylic polymer comprises a monomer selected from the group consisting of 2-phenylethyl acrylate and 2-phenylethyl methacrylate.

* * * * *